(12) United States Patent
Wei et al.

(10) Patent No.: US 6,398,961 B1
(45) Date of Patent: Jun. 4, 2002

(54) DEVICE AND METHOD FOR SENSING LOW LEVEL IODINE IN AQUEOUS SOLUTION

(75) Inventors: Guang-jong Jason Wei, Mendota Heights; Louis Mark Holzman, St. Paul, both of MN (US)

(73) Assignee: Ecolab Inc., St. Paul, MN (US)

( * ) Notice: Subject to any disclaimer, the term of this patent is extended or adjusted under 35 U.S.C. 154(b) by 0 days.

(21) Appl. No.: 09/619,879

(22) Filed: Jul. 20, 2000

(51) Int. Cl.[7] ............................................... B01D 11/04
(52) U.S. Cl. ...................... 210/634; 210/94; 210/96.1; 210/511; 210/745; 210/804; 422/82.05; 436/125; 436/164; 436/178
(58) Field of Search .................... 210/94, 96.1, 511, 210/513, 634, 745, 764, 800, 804, 805, 806; 436/101, 124, 125, 164, 178; 422/82.05

(56) References Cited

U.S. PATENT DOCUMENTS

| | | |
|---|---|---|
| 2,759,869 A | 8/1956 | Sutton et al. |
| 3,029,183 A | 4/1962 | Winicov et al. |
| 3,150,096 A | 9/1964 | Schmidt et al. |
| 3,215,627 A | 11/1965 | Tools |
| 3,232,869 A | 2/1966 | Gard |
| 3,525,696 A | 8/1970 | Schmidt et al. |
| 3,650,965 A | 3/1972 | Cantor et al. |
| 4,388,231 A | 6/1983 | Person |
| 4,575,491 A | 3/1986 | Pollack et al. |
| 4,752,740 A | 6/1988 | Steininger |
| 4,801,886 A | 1/1989 | Steininger |
| 4,946,673 A | 8/1990 | Pollack et al. |
| 5,130,033 A | 7/1992 | Thornhill |
| 5,310,549 A | 5/1994 | Bull |
| 5,832,972 A | 11/1998 | Thomas et al. |
| 5,919,374 A | 7/1999 | Harvey et al. |
| 5,962,029 A | 10/1999 | Duan et al. |

Primary Examiner—Joseph W. Drodge
(74) Attorney, Agent, or Firm—Vidas, Arrett & Steinkraus, P.A.

(57) ABSTRACT

The present invention relates to a method and to a device for sensing low levels of iodine in an aqueous solution by using an extraction procedure whereby iodine from the aqueous solution is extracted into a substantially water-insoluble organic phase, and testing measuring the concentration of iodine in the organic phase using optical absorption techniques. The measured concentration of iodine can then be equated with concentration of iodine or iodine in the aqueous solution.

33 Claims, 2 Drawing Sheets

DEVICE AND METHOD FOR SENSING LOW LEVEL IODINE IN AQUEOUS SOLUTION

FIELD OF THE INVENTION

The present invention relates to a method and to a device for sensing low levels of iodine in an aqueous solution by using an extraction procedure whereby iodine from the aqueous solution is extracted into a substantially water-insoluble organic phase, and testing the color of the organic phase using optical absorption techniques.

BACKGROUND OF THE INVENTION

It is a generally recognized principle that water must be effectively treated before it can be utilized in swimming pools, hot tubs and spas, particularly when the pools, etc. are used by segments of the general public. Swimming pools, hot tubs and spas are highly susceptible to rapid micro-organism growth and that they can rapidly become extremely hazardous to users thereof unless the water is effectively and continuously treated against micro-organisms.

One of the most widely recognized methods of treating water against micro-organisms to render the water safe for human consumption and/or use in swimming pools, spas, etc. is to add chlorine (normally in the form of a hypochlorite salt or chlorine gas) to the water. However, chlorine has been found to have an unpleasant or objectionable odor and can cause skin irritations and serious eye irritations to users of pools, spas, etc, an effect which is particularly noticeable in indoor swimming pools, hot tubs and spas. The use of chlorine can also lead to the formation of chloramines. Further, chlorine is sensitive to organic soils.

Due to the objectionable physical properties of chlorine a number of alternate water treatment systems have been developed in recent years, including the use of bromine and/or iodine.

It is known that iodine may be effectively used in small concentrations to impart desirable antimicrobial activity for various applications. For instance, U.S. Pat. No. 2,759,869, U.S. Pat. No. 3,029,183, U.S. Pat. No. 3,650,965, U.S. Pat. No. 3,525,696 and U.S. Pat. No. 3,150,096 all disclose aqueous liquid or said iodine use dilution compositions for various uses.

Further, it is known that iodine may be used in small concentrations to disinfect pools, hot tubs, spas and the like, and is typically formed by mixing oxidizable halide salts with an oxidizing agent. Active oxidizers include hydrogen peroxide, hypochlorite, peracid, chlorine dioxide, chlorate, chlorite, iodophors, and so forth. The iodide salt and oxidant may be mixed with a compound which is capable of forming a complex in order to improve the solubility of the iodine. An example of one such process is described in U.S. Pat. No. 5,130,033. Iodine may exist in the water as $I^-$, $I_2$ and $I_3^-$. U.S. Pat. No. 4,946,673 discusses the use of germicidal iodine. It is the $I_2$ species which act effectively against microbes.

These sanitizing systems must, however, be maintained at proper levels. Too much iodine, for instance, can result in an aesthetically objectionable color in the water. Too little iodine can result in the rapid growth of micro-organisms which, when once established, can rapidly propagate to unsafe levels. In order to maintain the iodine at proper levels, it is therefore necessary to have an easy and effective means of monitoring the concentration of iodine in the water. This can be a problem due to the low concentration of iodine employed.

Iodine is typically employed at concentrations of a few parts per million or less. For instance, U.S. Pat. No. 3,215,627 discloses a method for use in the disinfection of swimming pools. The range of free molecular iodine that is generated according to the method of the '627 patent is between 0.2 and 0.4 ppm. U.S. Pat. No. 3,232,869 describes a method for purifying and disinfecting aqueous liquids with free molecular iodine wherein the iodine is provided by quantitatively oxidizing iodide ion into free molecular iodine with persulfates at a pH between 7 and 8. The patent requires the use of a stoichiometric amount of either iodide or persulfate to yield a free iodine concentration of 0.1 to 1.0 ppm of free molecular iodine. It is important that the concentration be maintained within its optimal use concentration range. However, due to the extremely low concentration levels it can be difficult to accurately detect its presence.

One option for detecting iodine is the oxidation-reduction potential (ORP) sensor found in U.S. Pat. No. 4,752,740. There are a couple of disadvantages to using this method, however. One disadvantage is that, because it depends on the ratio of an oxidized species over a reduced species, it requires the detection of more than one species. Consequently, this method is not unique to the species that actually kills the bacteria, for example the iodine species, but rather the measurement of the iodine species is embedded in the ratio. Furthermore, this method is susceptible to changes in pH. Its usefulness is therefore limited when employed in swimming pools, spas, hot tubs, etc.

Another method that may be used is the hand titration method in which thiosulfate is used to manually titrate the aqueous solution. Iodine is readily reduced by thiosulfate to iodide. The end point is indicated by the disappearance of the distinct blue color of the starch-iodine complex. This type of method is usually supplied as a test kit in which batches of water are tested, rather than a continuous monitoring system. Titration of iodine is discussed in U.S. Pat. No. 4,946,673. Automation of this procedure for continuous monitoring capabilities is complicated and expensive.

Another method is the optical absorption of the aqueous solution directly. However, this method is highly susceptible to low signal and high noise.

Each of these methods lacks the sensitivity required for accurately detecting low levels of iodine in the range of fractions of a part per million to a few parts per million.

The present invention relates to a novel process for the detection of free iodine in pools, spas, hot tubs and the like that is easier to use, is specific to the free iodine concentration, and that is not susceptible to the presence of other species and to pH changes.

SUMMARY OF THE INVENTION

The present invention relates to a process whereby low levels of iodine may be easily and readily detected. The iodine is extracted from an aqueous environment, for example a chemically treated pool, into a substantially water-insoluble organic phase whereby the iodine concentration is determined through the use of optical absorption.

In one aspect, the present invention relates to a novel method of sensing low levels of iodine in an aqueous solution comprising the steps of providing a substantially water-insoluble liquid organic phase trapped in a container by its low specific gravity and contacting the aqueous solution with the substantially water-insoluble liquid organic phase thereby distributing iodine between both the aqueous phase and the substantially water-insoluble organic phase.

The contacting step may be accomplished by feeding the aqueous solution into the substantially water-insoluble organic phase. The water is subsequently separated through the natural forces of gravity, and by the fact that it is immiscible with the organic phase. The water may then be flowed into a waste stream, or optionally recycled back into its point of origination, i.e. a pool, spa, or hot tub, for instance. The container holding the substantially water-insoluble organic phase is transmissive to light at a wavelength absorbed by iodine in the substantially water-insoluble organic phase, allowing the amount of iodine in the substantially water-insoluble organic phase to be quantified by optical absorption. The amount of iodine in the aqueous phase can then be calculated using a known distribution coefficient or the ratio of iodine in the organic phase to iodine in the aqueous phase.

The present invention may be incorporated into a system wherein it is a continuous method of sensing iodine, or alternatively, the present invention can be used in a batch mode for detecting the amount of iodine.

A batch method finds use in instances where a composition, e.g. a concentrate, is being diluted for use and one wishes to determine the concentration of the diluted solution. A batch is also useful where the body of water from which the reading is taken is relatively small, i.e. less than 20 gallons, for instance.

In another aspect, the present invention relates to a device for continuously analyzing low levels of an iodine complex in an aqueous solution such as for a pool, spa or the like, the device comprising a container that is transmissive to light at a wavelength absorbed by iodine in the substantially water-insoluble organic phase; a substantially water-insoluble liquid organic phase in the container, the container configured in such a manner that the organic phase is above the aqueous phase in the container; a means for providing a stream of the aqueous solution to be analyzed into the organic phase; a photo detector for continuously measuring the optical absorption of said liquid organic phase at about 480 to about 560 nm wavelength; and an exiting means for the aqueous solution.

In another aspect, the present invention relates to a method of determining the concentration of a cleaning, bleaching or sanitizing composition after dilution with an aqueous liquid. This involves adding to the composition, a known amount of an iodide tracer, contacting the diluted composition with an aqueous solution comprising a sufficient amount of an oxidative compound thereby converting said iodide to iodine, contacting the iodine-containing aqueous solution with a water-insoluble liquid organic phase thereby extracting said iodine into said liquid organic phase. The concentration of iodine in the organic phase can then be measured using an optical absorption device, and the concentration of iodine can be equated with the concentration of iodide and the concentration of the diluted solution thus determined.

In yet another aspect of the invention, low levels of an oxidant can be detected by adding iodide ion to the aqueous solution, and the iodine thus formed can be determined in the same manner.

DETAILED DESCRIPTIONS OF THE PREFERRED EMBODIMENTS

The process of the present invention involves the extraction of free iodine from an aqueous solution into a substantially water-insoluble organic phase whereby a photo detector may measure the optical absorption of the organic phase at a wavelength that is indicative of the iodine concentration. The iodine is more soluble in the organic phase. Further, the extraction of iodine from a relatively large body of aqueous solution, into a relatively small amount of a water-immiscible organic phase combined with the greater solubility of iodine in the organic phase allows enrichment of the organic phase thereby making optical measurements more accurate and the readings less susceptible to noise. Using the present invention, extraction can be conducted either continuously, or in a batch mode.

Figure 1:
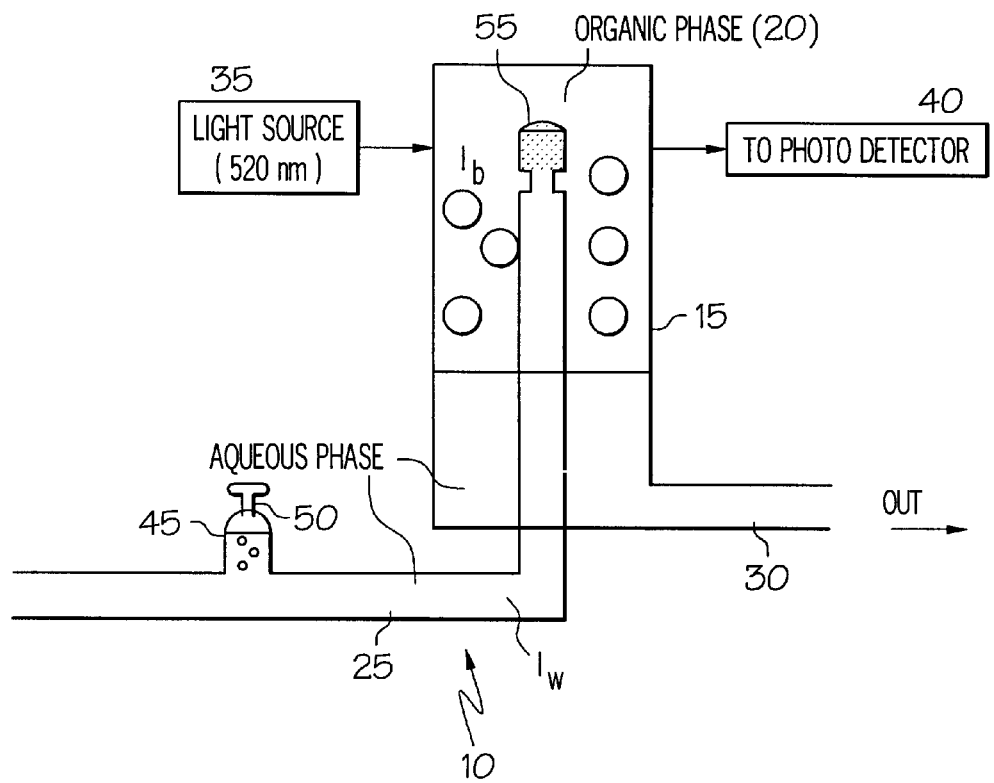
FIG. 1 is a perspective view of an extraction/photo detection device for measuring the concentration of iodine in aqueous solutions.

FIG. 1 illustrates generally at (10) a device for the extraction and photo detection of iodine. An extraction container (15) contains the water-insoluble organic phase (20). An inlet (25) delivers aqueous solution into the organic phase (20). Optionally attached to the inlet is a bubbler device (45) for trapping air. a valve (50) is attached to the bubbler (45) for releasing the air. The device serves to prevent air from accumulating at the top of the extraction container (15) above the organic layer (20).

Also optionally attached to the end of the inlet is a dispersing frit (55). The frit may be added to increase the contact area for the aqueous solution by dispersing the aqueous solution into the organic phase more. The porosity of the frit allows the aqueous solution to be distributed more evenly throughout the organic phase (20) which is held in container (15). This leads to a more rapid extraction process. The aqueous phase, being more dense than the organic layer settles to the bottom of the container (15) and flows out through outlet (30). An equilibrium is reached between the now iodine-containing organic phase and the iodine-containing aqueous phase. a light source (35) is supplied whereby light at a wavelength of about 520 nm shines through the container (15) which is transmissible to light, and the optical absorption is measured by photo detector (40). The optical signal is proportionally to the path length and consequently, the path length may be increased in order to increase the sensitivity of the optical device. This might, for instance, involve increasing the width of the top of the container (15) through which the light is transmitted and absorption recorded.

The optical absorption is directly proportional to the concentration of iodine in the organic phase, which based on the equilibrium relationship between iodine in the organic phase and iodine in the aqueous solution may then be used to determine the concentration of iodine in the aqueous solution. The equilibrium constant will depend on the composition of the organic phase. The organic phase should be selected so that the iodine is more readily soluble in the organic phase than in the aqueous solution.

Figure 2:
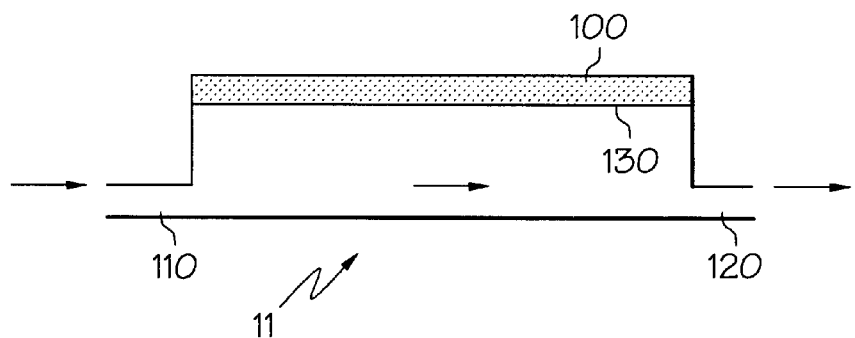
FIG. 2 is a perspective view of an alternative embodiment of an extraction/photo detection device for measuring the concentration of iodine in aqueous solution in which contact occurs at a laminar boundary instead of a dispersion.

FIG. 2 illustrates generally at (11) an alternative embodiment of the device of the present invention. FIG. 2 employs a container (150) in which a laminar or thin layer (100) of organic solution forms. The aqueous solution flows past the laminar layer from an inlet line (110), contacting the organic solution at boundary (130) of the thin layer in the container and then flows out of the container (150) into an outlet (120). The iodine, being more soluble in the organic solution, is extracted from the aqueous solution. Equilibrium is reached more slowly with this type of device versus the device illustrated in FIG. 1 in which the aqueous solution is forced into the organic phase, and may also be dispersed therein.

Figure 3:
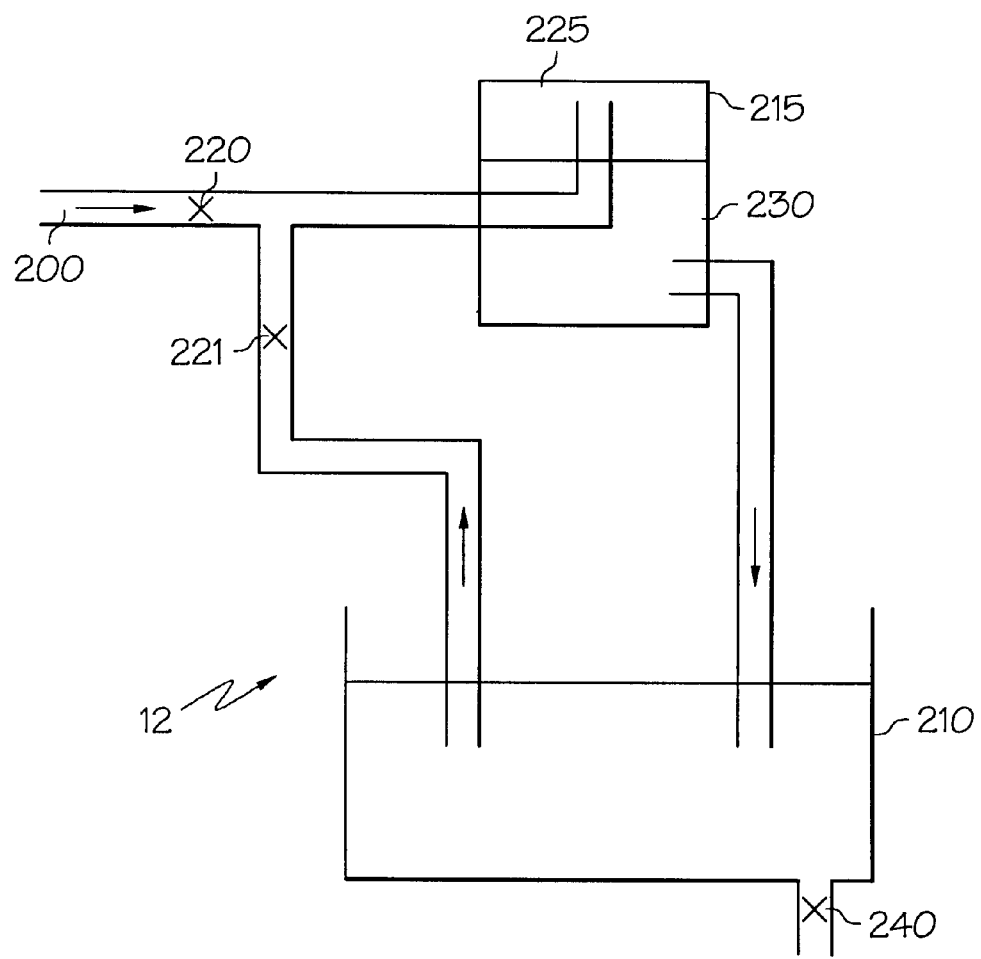
FIG. 3 is a perspective view of a batch mode extraction/photo detection device for measuring the concentration of iodine in aqueous solutions. This device is for measuring iodine levels in small bodies of water in which the water may be recycled.

FIG. 3 illustrates generally at (12) a batch processing device for detecting low levels of iodine. This device is particularly useful where the body of water to be tested is quite small, for instance, about 20 gallons of water (about 75 liters) or less. The aqueous solution is fed through the inlet (200) and into a container (215) which holds an organic layer, such as hexane, (225), and the aqueous layer (230), is shown at the bottom of the container. a valve (220) may be placed near the inlet (200) for controlling the amount of water taken from the source. The aqueous solution may be charged into a reservoir (210) holding from about 2–10 liters of solution and recirculated through the container (215). Once the iodine in the aqueous phase and the iodine in the organic phase has reached its equilibrium and the final concentration is recorded, the batch may be drained through valve (240). This arrangement may also be used in a continuous mode with valves (220) and (240) open and valve (221) closed.

The iodine sensor device works on the principle that the iodine is much more soluble in the chosen organic phase, than in the aqueous solution. Iodine will thus concentrate more in the organic phase improving the accuracy of the optical absorption measurement. One of the problems associated with the direct optical absorption measurement of iodine in the aqueous phase, particularly in larger aqueous systems such as a pool or spa where the iodine level is typically very low, for instance, from a fraction of a part per million to a few parts per million, is that the accuracy is decreased due to low signal and high noise.

The sensor response time of the present invention, (T), depends on flow rate (q), flow time (t), mixing pattern/contact area (A), rate of $I_2$ transport (k) across water/organic phase boundary, and the volume of organic phase $V_o$. The principles of mass conservation may be utilized to determine sensor response time, or how quickly equilibrium may be reached between the aqueous phase, and the water-immiscible organic phase:

$$V (dI_o/dt) = -(I_o - I_w) kqA$$

where $I_o$ is the iodine concentration in the water-immiscible organic phase, and $I_w$ is the iodine concentration in water; then $$(I_o - I_w)_t = (I_o - I_w)_{t=o} (1 - \exp(-(kqA/V)t))$$

$I_o$ changes exponentially with a response time $T = V (\ln 2)/kqA$.

The organic phase is preferably comprised of an organic solvent(s) that has a high partitioning ratio, low viscosity, is colorless, non-flammable, has low volatility, and has a low solubility in water. Preferably, the partitioning ratio between the solvent and the aqueous phase is about 10 or more, such as from about 10 to about 100, and preferably from about 20 to about 50. It is undesirable that the organic phase form an emulsion or foam with water. The toxicity rating, LD 50, of the solvent is also a consideration, and a solvent with a low LD 50 is preferred. The water-insoluble organic phase is preferably composed of a substantially water-insoluble alkanes including decane, dodecane, hexadecane, hexane, mineral oil, and so forth.

Alternatively, a field test kit may be devised for testing the iodine level manually. The field test method requires that a set amount of water-insoluble solvent is mixed with a relatively larger volume of aqueous solution. Preferably the ratio of solvent to aqueous solution is at least about 1:50, and preferably about 1:100 to 1:1000. The large ratio is required to keep the loss of iodine from the aqueous solution to a minimum to ensure that it is the initial uninterrupted iodine concentration that is being detected. If too much iodine is removed from a small volume of water, the concentration of iodine in the water can be affected. Most of the iodine will be extracted into the organic phase which will appear on the top. The color of the organic phase can be easily measured using a spectrophotometer, or can be detected visually against a color grading standard which may be in the form of a chart.

The present invention may be modified for use in testing and control of oxidative sanitizers in industrial applications such as clean-in-place in dairy, food, beverage, pharmaceutical and cosmetic plants, and so forth. Oxidative sanitizers for use in such systems include chlorine, hypochlorite, peracids, chlorine dioxide, chlorate, chlorite, iodophor products, and so forth. Using this method, a sufficient amount of iodide is injected into the test solution upstream of the extracting organic phase. The oxidative sanitizer converts iodide to iodine, which is then extracted into the organic phase for absorption measurements as described above.

A tracer may also be added to a cleaner or sanitizer product to prevent improper use of solutions, or the use of incorrect solutions. The tracer iodide is added to a product that is used in lock-out dispensers, for instance. Such a device is described in U.S. Pat. No. 5,832,972 incorporated by reference herein in its entirety. The lock-out member prevents the use of an incorrect bottle while dispensing the use solution thus preventing the unauthorized use of such dispensers. Typically, these dispensers either hold concentrates, or draw the concentrate from a large storage container, and are used in institutional or industrial locations where large quantities of materials are used.

These concentrates may then be diluted for use in general purpose cleaning and sanitizing compositions such as hard surface cleaners, glass cleaners, window cleaners, floor cleaners, sink cleaners, tile cleaners, drain cleaners and openers, cleaners for food preparation units, sanitizers, disinfectants, odor counteractants, and so forth. These devices may be used in the dairy industry for clean-in-place, in the food industry for cleaning solutions, and so forth.

A small amount of tracer iodide is added to the sanitizing or disinfecting product. The tracer is oxidized on a side stream attached to the dispenser using oxidants according to the following equation:

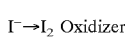

$$I^- \rightarrow I_2 \text{ Oxidizer}$$

The concentration of $I_2$ may then be determined through the use of optical absorption readings. A positive reading would indicate that the correct product, i.e. that with the tracer iodide, is being used. The oxidants useful to the present invention include chlorine, hypochlorite, peracids, chlorine dioxide, chlorate, chlorite, iodophor products, and so forth.

The present invention may also be used to determine the concentration of sanitizing compositions after dilution with an aqueous solution. In this aspect of the invention, a known amount of tracer iodide is added to the composition. The diluted solution is contacted with a sufficient amount of an oxidative compound to convert the iodide to iodine as shown in the equation above. The iodine-containing aqueous solution is then contacted with a water-immiscible liquid organic phase and the iodine is extracted into the organic phase. Again, the organic phase is selected so that the iodine is substantially more soluble in it than in the aqueous phase. The organic phase, now enriched with iodine, can then be measured using a photo detection device. Once the concentration of iodine in the organic phase is determined, that can be related to the tracer iodide concentration which can subsequently be used to determine the concentration of the diluted solution. In this fashion one can determine if the concentrate has been diluted to its proper concentration.

The present invention may consequently find use in many applications where sanitizing solutions are employed. The invention finds utility in industrial operations where large quantities of such solutions are used including institutional health care settings, restaurant and food preparation facilities, food manufacturing and processing plants, large dairy operations, and so forth.

Specific applications where iodinated aqueous solutions may be used include in farm animal drinking water distribution networks; in disinfectants for use in the food processing industry; for fruit, vegetable and fish preservation; industrial or commercial cooling tower waters; for sewage and waste water treatment; as a nutrient iodine source for humans, livestock, fish and plants; and so forth.

EXAMPLES

Experiment 1

The concept of a continuous flow monitoring device was tested using 10 cc of hexane in a 30 cc gas impinger in an inverted orientation. An iodine test solution (500 cc) with a concentration of about 0.5 ppm, was pumped into the hexane layer through a glass frit at 50 cc/min. a visible pink color appeared in the hexane layer. Pumping 500 cc of water into the impinger restored the hexane layer to a clear, colorless liquid.

Experiment 2

The concept of a manual test kit was verified by adding 2 ml of hexane to 1 liter of iodine test solution in a volumetric flask. The flask was inverted several times with gentle shaking. The hexane layer turned a visible pink color, and was allowed to separate from the aqueous solution by gravity. The optical absorption of the hexane layer at 520 nm was measured using a Spectronics Genesys 5.

The experiment was accomplished using various concentrations of iodine sanitizing solution. The results are found in the following table.

TABLE 1

| Concentration of Iodine Solution (ppm) | Absorption at ~520 nm |
|---|---|
| 0.3 | 0.029 |
| 0.5 | 0.041 |
| 1.0 | 0.068 |

Experiment 3

The concentration ratio or distribution constant of iodine in hexane and water was determined using the following procedure. Iodine, 11.3 mg, was dissolved in 60 ml (about 39.6 g) of hexane. The concentration was 285 ppm. The absorbance of the hexane solution was determined to be 0.702 at a wavelength of 520 nm. This corresponded to 406 ppm iodine per 1.0 absorbance.

The above iodine/hexane solution, 40 ml (about 26.4 g), was mixed with 160 ml (160 g) of water. The solution was rigorously mixed to reach equilibrium. The mixture was then allowed to separate in a hexane layer (top) and an aqueous layer (bottom). The absorbance of the hexane layer was measured at 520 nm and determined to be 0.599. The distribution Constant, DC, was calculated using the following equation:

$$DC=(0.599/26.4)\div[(0.702-0.599)\div160]=35.3$$

This ratio, in combination with the 406 ppm iodine per 1.0 absorbance, can then be used to calculate the iodine concentration in the aqueous phase after extraction into the hexane phase (or any organic phase selected) using the following equation:

$$\text{ppm iodine in water}=11.5\times(\text{absorbance of hexane extract})$$

Experiment 4

Alternate organic solvents were tested for extraction of $I_2$. An aqueous solution (200 g) of 10 ppm $I_2$ was placed in a bottle along with 10 g of the organic solvent. The solution was then shaken and the organic solvent allowed to separate from the water. The absorption spectra of the various organic phases was measured. The results are found in Table 2.

TABLE 2

| Solvent | Absorption at ~520 nm |
|---|---|
| hexane | 0.250 |
| hexadecane | 0.276 |
| mineral oil | 0.299 |

As illustrated by the above data, a higher molecular weight alkane exhibits a higher distribution constant.

Experiment 5

A frit apparatus as illustrated by FIG. 1, was used to disperse aqueous iodine-containing solution into a 10 ml water-immiscible hexane organic phase (hexadecane may be substituted). Using a frit resulted in good dispersion and pink color was visible after approximately 1 liter of aqueous solution in 10 minutes.

Experiment 6

The same device as in FIG. 1, but without the optional frit apparatus, was used to disperse aqueous iodine-containing solution into a water-immiscible hexane organic phase. Pink color was visible in the organic phase after 1 liter of aqueous solution had been flowed through in 10 minutes. The pipet device exhibited no substantial loss of hexadecane after two hours.

Experiment 7

A planar interface apparatus as illustrated in FIG. 2 was used for iodine extraction. An aqueous iodine-containing solution was routed through the flowcell with a hexadecane organic layer floating on the top and the aqueous solution flowing on the bottom. No pink color became apparent in the hexadecane layer after 1 liter of aqueous solution passed through in 10 minutes. A pink color was visible after an hour of operation. A much longer extraction time is required due to the smaller contact area found in this device. However, this device may find use where the amount of time required for extraction/detection is not of issue.

We claim:

1. A method of sensing low levels of iodine in an aqueous solution comprising the steps of:
   a) providing a substantially water-insoluble liquid organic phase trapped in a container by buoyancy, said container being transmissive to light at a wavelength absorbed by iodine in the substantially water-insoluble organic phase;
   b) contacting said aqueous solution and said liquid organic phase whereby said iodine from said aqueous phase is distributed between said aqueous solution and said liquid organic phase;
   c) separating said aqueous solution by gravity; and
   d) quantifying said iodine content in said organic phase by optical absorption.

2. The method of claim 1 wherein said organic phase comprises an alkane.

3. The method of claim 1 wherein said organic phase is mineral oil.

4. The method of claim 1 wherein said organic phase is colorless.

5. The method of claim 1 wherein said organic phase has low solubility in water.

6. The method of claim 1 wherein the partitioning ratio between said organic phase and said aqueous solution is greater than about 10.

7. The method of claim 2 wherein said alkane is selected from the group consisting of decane, dodecane, hexane, hexadecane, and mixtures thereof.

8. The method of claim 1 wherein said quantifying is conducted in a batch mode.

9. The method of claim 1 wherein said quantifying is conducted in a continuous mode.

10. The method of claim 1 wherein said optical absorption is conducted by optical absorption in the visible range at a wavelength of about 480–560 nanometers.

11. The method of claim 10 wherein said optical absorption is conducted at 520 nanometers.

12. The method of claim 1 wherein said contacting step is accomplished by feeding said aqueous solution into said liquid organic phase.

13. The method of claim 1 wherein after said contacting step, said organic phase and said aqueous solution are mixed together by shaking.

14. The method of claim 13 wherein said organic phase and said aqueous solution are allowed to separate by gravitational forces.

15. The method of claim 1 wherein an equilibrium constant is established between iodide in the organic phase and iodine in the aqueous solution which is from about 20 to about 40.

16. The method of claim 1 wherein said aqueous solution is water from a pool, spa or hot tub.

17. A method of sensing complexed iodine in aqueous liquids, comprising the steps of:
   a) contacting a stream of an aqueous liquid with a substantially water-insoluble predetermined quantity of an immobile liquid organic phase whereby said iodine is extracted into said organic phase, an equilibrium being established between iodine in the aqueous liquid and iodine in the organic phase;
   b) measuring the iodine concentration of the organic phase at a wavelength indicative of iodine concentration; and
   c) determining the iodine concentration in the aqueous liquid in accordance with a predetermined relationship between said optical absorption of the organic phase with the concentration of iodine in the aqueous liquid.

18. The method of claim 17 further comprising the step of recycling said aqueous liquid.

19. The method of claim 17 wherein said contacting step is accomplished by dispersing said aqueous liquid into said organic phase to increase the contact between said aqueous liquid and said organic phase thereby improving extraction efficiency.

20. A method for sensing and control of the concentration of an acqueous based oxidative sanitizer comprising the steps of:
   a) injecting an aqueous solution comprising iodide into a side stream of said aqueous based oxidative sanitizer solution whereby said iodide is converted to iodine;
   b) contacting said mixed aqueous solution comprising iodine with a liquid organic phase whereby said iodine is extracted into said liquid organic phase;
   c) separating said liquid organic phase from said aqueous solution by gravitational forces;
   d) measuring the iodine concentration in said organic phase by optical absorption; and
   e) equating said iodine concentration with said oxidative sanitizer concentration using a pre-determined stoichiometric ratio.

21. The method of claim 20 wherein said oxidative sanitizer is selected from the group consisting of chlorine, hypochlorite, peracids, chlorine dioxide, chlorate, chlorite, iodophors, and mixtures thereof.

22. A method of determining the use concentration of a cleaning composition prepared from a concentrate comprising the steps of:
   a) adding a known amount of tracer iodide to the concentrate;
   b) diluting said concentrate with water to a use concentration;
   c) contacting said diluted composition with an aqueous solution comprising a sufficient amount of an oxidative compound to convert said iodide to iodine;
   d) contacting said aqueous solution of step b) with a water-insoluble liquid organic phase thereby extracting said iodine into said liquid organic phase; and
   e) measuring said iodine concentration using an optical absorption device;
   f) determining the use concentration of the cleaning composition from the neasured concentration of iodine.

23. A device for analyzing low levels of an iodine complex in an aqueous liquid comprising:
   a) a container transmissive to light at a wavelength absorbed by iodine in a substantially water-insoluble liquid organic phase;
   b) a substantially water-insoluble liquid organic phase in said container, said container configured so that said organic phase is above said aqueous phase in said container;
   c) a flow system configured and arranged for providing a stream of said aqueous liquid, and for bringing said aqueous liquid into contact with said organic phase in said container, the flow system including an exit configured and arranged for removing said stream of aqueous liquid from the container without removing said organic phase; and
   d) a photo detector operable for measuring the optical absorption of said liquid organic phase at a wavelength of about 480 to about 560 nm.

24. The device of claim 23 wherein said organic phase comprises an alkane.

25. The device of claim 23 wherein said organic phase is mineral oil.

26. The device of claim 23 wherein said organic phase is colorless.

27. The device of claim 23 wherein said organic phase has low solubility in water.

28. The device of claim 23 wherein the partitioning ratio between said organic phase and said aqueous solution is greater than about 10.

29. The device of claim 23 wherein said alkane is selected from the group consisting of decane, dodecane, hexane, hexadecane, and mixtures thereof.

30. The device of claim 23 wherein said optical absorption is conducted at 520 nanometers.

31. The device of claim 23 wherein said organic phase and said aqueous solution are allowed to separate by gravitational forces.

32. The device of claim 23 wherein an equilibrium constant is established between iodide in the organic phase and iodine in the aqueous solution which is from about 20 to about 40.

33. The device of claim 23 wherein said stream of aqueous solution is water from a pool, spa or hot tub.

* * * * *